(12) United States Patent
Yachia et al.

(10) Patent No.: US 10,039,907 B2
(45) Date of Patent: Aug. 7, 2018

(54) DEVICE, SYSTEM, AND METHOD FOR RELEASING SUBSTANCES IN A BODY CAVITY

(75) Inventors: Daniel Yachia, Herzliya (IL); Eran Hirszowicz, Ramat Gan (IL); Dov Dvir, Havazzelet-Hasharon (IL)

(73) Assignee: INNOVENTIONS LTD., Caesarea (IL)

( * ) Notice: Subject to any disclaimer, the term of this patent is extended or adjusted under 35 U.S.C. 154(b) by 627 days.

(21) Appl. No.: 12/385,590

(22) Filed: Apr. 13, 2009

(65) Prior Publication Data

US 2010/0016834 A1 Jan. 21, 2010

Related U.S. Application Data

(60) Provisional application No. 61/071,120, filed on Apr. 14, 2008.

(51) Int. Cl.
*A61M 31/00* (2006.01)
*A61M 25/10* (2013.01)
*A61M 25/06* (2006.01)

(52) U.S. Cl.
CPC ...... *A61M 31/002* (2013.01); *A61M 25/1011* (2013.01); *A61M 25/0662* (2013.01); *A61M 25/1002* (2013.01); *A61M 2025/1013* (2013.01)

(58) Field of Classification Search
CPC .. A61M 2025/0076; A61M 2039/0646; A61M 25/10186; A61M 2025/1015; A61M 25/1006; A61M 3/0295; A61M 29/00
USPC .... 604/101.01, 101.02, 103.01, 103.02, 517; 623/23.65–23.67
See application file for complete search history.

(56) References Cited

U.S. PATENT DOCUMENTS

| | | | | |
|---|---|---|---|---|
| 3,707,151 A | * | 12/1972 | Jackson | A61M 16/04 128/207.15 |
| 3,726,283 A | * | 4/1973 | Dye | A61M 25/0069 604/247 |
| 3,889,686 A | * | 6/1975 | Duturbure | A61M 25/00 604/102.03 |
| 4,227,533 A | * | 10/1980 | Godfrey | A61M 25/0075 604/247 |
| 4,423,725 A | * | 1/1984 | Baran | A61B 17/22 128/207.15 |
| 4,545,367 A | * | 10/1985 | Tucci | A61B 17/12109 128/898 |

(Continued)

FOREIGN PATENT DOCUMENTS

WO 2004/041124 A1 5/2004

*Primary Examiner* — Bhisma Mehta
*Assistant Examiner* — Matthew A Engel
(74) *Attorney, Agent, or Firm* — Vorys, Sater, Seymour & Pease LLP; Ari Zytcer (57) ABSTRACT

An implantable device for releasing one or more substances into a body cavity such as a urinary bladder, is provided. The device includes an inner balloon located within an outer balloon so as to define a lumen between the outer and inner balloons. A first valve is used for filling the lumen; and a second valve is used for filling the inner balloon. The device is delivered to the body using a delivery catheter. The inner portion is filled with the substance or substances to be released into the body cavity. The outer balloon is filled with a substance that is chosen to impart a desired specific gravity to the device. The substances to be released may be contained in particles coated with a soluble coating. The particles may be in suspension or embedded in a matrix.

14 Claims, 9 Drawing Sheets

(56) References Cited

U.S. PATENT DOCUMENTS

| | | | | |
|---|---|---|---|---|
| 4,598,707 A * | 7/1986 | Agdanowski | A61M 25/1018 | 128/207.15 |
| 4,696,667 A * | 9/1987 | Masch | | 604/22 |
| 4,929,235 A * | 5/1990 | Merry | A61M 39/0606 | 137/849 |
| 4,960,412 A * | 10/1990 | Fink | A61M 39/0606 | 604/167.04 |
| 4,994,033 A * | 2/1991 | Shockey | A61F 2/82 | 604/101.02 |
| 5,035,705 A * | 7/1991 | Burns | A61M 25/0075 | 604/913 |
| 5,085,636 A * | 2/1992 | Burns | A61M 25/0075 | 604/913 |
| 5,217,434 A * | 6/1993 | Arney | A61M 25/0054 | 604/103.1 |
| 5,221,260 A * | 6/1993 | Burns | A61M 25/0075 | 604/913 |
| 5,269,755 A * | 12/1993 | Bodicky | A61M 25/0017 | 604/103.01 |
| 5,330,497 A * | 7/1994 | Freitas | A61B 17/34 | 604/164.12 |
| 5,360,403 A * | 11/1994 | Mische | A61M 25/0075 | 604/101.02 |
| 5,520,646 A * | 5/1996 | D'Andrea | A61M 25/10 | 604/103.1 |
| 5,536,252 A * | 7/1996 | Imran | A61M 25/1011 | 604/101.02 |
| 5,795,331 A * | 8/1998 | Cragg | A61B 17/12022 | 604/103.01 |
| 6,132,397 A * | 10/2000 | Davis | A61B 17/12109 | 604/101.02 |
| 6,254,570 B1 * | 7/2001 | Rutner | A61M 25/0017 | 604/101.01 |
| 6,368,317 B2 * | 4/2002 | Chang | G02B 3/12 | 141/105 |
| 6,746,465 B2 * | 6/2004 | Diederich | A61M 29/02 | 604/101.02 |
| 7,052,507 B2 * | 5/2006 | Wakuda | A61M 25/10 | 604/104 |
| 7,220,252 B2 * | 5/2007 | Shah | A61M 25/1011 | 604/101.02 |
| 7,410,480 B2 * | 8/2008 | Muni | A61B 5/411 | 604/509 |
| 7,708,716 B2 * | 5/2010 | Shah | A61M 25/1011 | 604/101.02 |
| 7,909,844 B2 * | 3/2011 | Alkhatib | A61M 25/0043 | 604/99.01 |
| 7,922,691 B2 * | 4/2011 | Kletschka | A61B 17/22032 | 604/96.01 |
| 7,942,850 B2 * | 5/2011 | Levit | A61M 25/1002 | 604/103.07 |
| 8,075,586 B2 * | 12/2011 | Kletschka | A61B 17/22032 | 606/200 |
| 8,088,121 B2 * | 1/2012 | Nishide | A61M 25/0054 | 604/102.02 |
| 8,197,505 B2 * | 6/2012 | Hirszowicz | A61M 25/1006 | 606/194 |
| 8,366,733 B2 * | 2/2013 | Gabel | A61B 17/00491 | 606/192 |
| 8,562,560 B2 * | 10/2013 | Adams | A61J 15/0042 | 604/103.09 |
| 8,597,240 B2 * | 12/2013 | Davies | A61M 25/1006 | 604/96.01 |
| 8,617,045 B2 * | 12/2013 | Salama | A61F 2/0009 | 600/29 |
| 8,771,161 B2 * | 7/2014 | Sutton | A61N 5/1015 | 600/3 |
| 2004/0131808 A1 * | 7/2004 | Schoenle | A61M 25/0045 | 428/35.7 |
| 2005/0015047 A1 * | 1/2005 | Shah | A61M 25/1011 | 604/101.02 |
| 2005/0101941 A1 * | 5/2005 | Hakky | A61M 25/04 | 604/544 |
| 2005/0131442 A1 * | 6/2005 | Yachia | A61F 2/0027 | 606/185 |
| 2005/0234388 A1 * | 10/2005 | Amos et al. | | 604/8 |
| 2006/0106361 A1 * | 5/2006 | Muni | A61B 5/06 | 604/500 |
| 2007/0088380 A1 * | 4/2007 | Hirszowicz | A61M 25/1006 | 606/194 |
| 2007/0239110 A1 * | 10/2007 | Shah | A61M 25/1011 | 604/96.01 |
| 2008/0045781 A1 * | 2/2008 | Salama | A61F 2/0009 | 600/29 |
| 2008/0319424 A1 * | 12/2008 | Muni | A61B 5/06 | 604/890.1 |
| 2009/0187254 A1 * | 7/2009 | Deal et al. | | 623/23.7 |
| 2009/0254064 A1 * | 10/2009 | Boatman | A61M 25/1011 | 604/509 |
| 2009/0254114 A1 * | 10/2009 | Hirszowicz | A61M 25/104 | 606/194 |
| 2010/0016834 A1 * | 1/2010 | Yachia | A61M 31/002 | 604/509 |
| 2010/0234838 A1 * | 9/2010 | Watson | A61B 18/02 | 606/21 |
| 2011/0118546 A1 * | 5/2011 | Dillon | A61M 25/0075 | 600/106 |
| 2012/0203173 A1 * | 8/2012 | Davies, Jr. | A61M 25/1006 | 604/96.01 |
| 2012/0245608 A1 * | 9/2012 | Hirszowicz | A61M 25/104 | 606/159 |
| 2014/0039358 A1 * | 2/2014 | Zhou | A61N 7/022 | 601/3 |
| 2014/0081075 A1 * | 3/2014 | Salama | A61M 25/0017 | 600/31 |
| 2014/0277066 A1 * | 9/2014 | Schaeffer | A61M 25/1006 | 606/192 |
| 2015/0011827 A1 * | 1/2015 | Kinoshita | A61B 17/24 | 600/114 |

* cited by examiner

DEVICE, SYSTEM, AND METHOD FOR RELEASING SUBSTANCES IN A BODY CAVITY

This application claims the benefit of prior U.S. provisional patent application No. 61/071,120 filed Apr. 14, 2008, the contents of which is hereby incorporated by reference in its entirety.

FIELD OF THE INVENTION

This invention relates to medical devices, and more specifically to such devices for releasing substances in the body.

BACKGROUND OF THE INVENTION

There are many urinary tract conditions that are treated by delivering to the urinary bladder drugs or other substances, such as radioactive substances, and antibiotics. Such conditions include urinary incontinence, urinary tract infections, bladder tumors, and bladder dysfunctions. In order to obtain controlled release of a substance in the urinary bladder it is known to insert a device into the bladder that stores the substances and releases them slowly over time. WO 2004/041124 discloses a device comprising a balloon that is inflated inside the urinary bladder. The device also comprises an insert that is affixed to the balloon and that stores and releases substances into the bladder.

SUMMARY OF THE INVENTION

The present invention provides a device for releasing one or more substances in a body cavity such as a urinary bladder. The device of the invention comprises an inflatable balloon. In one embodiment, the balloon is configured to receive an insert containing the substances to be released into the body cavity. The substances diffuse out of the insert through the exposed surface of the insert into the cavity.

In one embodiment of the invention, the device comprises a balloon having a channel and an insert configured to be retained in the channel. The insert has one or more compartments for containing the one or more substances to be released. In one embodiment, the insert has groves on its surface to increase surface area of the insert available for diffusion of the substances from the compartment and for increasing the surface area of the insert to fluids in the cavity, such as urine in the case of the urinary bladder. In another embodiment, the insert has an amplified surface area by being shaped as an open-ended cylindrical shell, with the compartment contained within the wall of the shell. After delivery of the device to the body cavity, fluid in the cavity contacts the surface of the insert and substance stored in the compartment diffuse out of the compartment into the fluid.

In another embodiment, the device comprises an outer balloon having a central conduit and an inner expandable balloon with one or more compartments located in the interior of the outer balloon. After delivery of the device to the body cavity, the lumen of the inner balloon is filled with a fluid or dry material containing the substance or substances to be released into the cavity. The lumen between the inner and outer balloons is filled with a fluid having a specific gravity to allow the balloon to float or sink in the cavity fluid, as required in any application. The substances then diffuse out from the interior of the inner balloon though diffusion windows into the body cavity.

In one preferred embodiment, the substances to be released are contained in particles that are sized so as not to be able to diffuse out of the device. The particles are encapsulated with a biodegradable coating or capsule. The encapsulated particles are suspended in a liquid and injected in to the device. After delivery into the body cavity, the cavity fluid diffuses into the device and dissolves the biodegradable coating or capsule of the particles. The substances are thus liberated from the capsules or particles, and are thus released into the fluid. The substances diffuse in the fluid out of the device 10 and into the body cavity.

The device of the invention may optionally be configured to perform one or more additional functions in the body cavity such as imaging the cavity, measuring cavity volume, temperature and pressure, fluid composition, monitoring the cavity, or irradiating the cavity, for example as disclosed in WO 2004/041124. The device of the invention may further comprise a magnetizable portion in order to facilitate retrieval of the device from the body cavity.

Thus, in its first aspect, the invention provides an implantable device having an exterior surface for releasing one or more substances into a body cavity, comprising:
  (a) an outer balloon;
  (b) an inner balloon located within the outer balloon so as to define a lumen between the outer balloon and the inner balloon;
  (c) a first valve for filling the lumen; and
  (d) a second valve for filling the inner balloon.

In its second aspect, the invention provides a system for delivering a substance into a urinary bladder, the system comprising:
  (a) a device of the invention; and
  (b) a delivery catheter for delivering the device into a urinary bladder.

The invention further provides a method of releasing into a urinary bladder one or more substances comprising:
  (a) providing an implantable device of the invention;
  (b) delivering the device through the urethra to the bladder;
  (c) filling the outer balloon; and
  (d) filling the inner balloon with the one or more substances.

The invention also provides an implantable device for releasing one or more substances into a urinary bladder, the device comprising an expandable balloon having a toroidal shape defining a hole, and an insert having a longitudinal axis and capable of storing one or more compounds and releasing them into the bladder, configured to be received and secured in the hole, so as to allow a urine flow along the longitudinal axis.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

In the description below, an embodiment of the invention will be described for releasing substances into a urinary bladder, it being obvious to those skilled in the art that the system and method of the invention may be adapted to release a substance in any body cavity.

Figure 1:
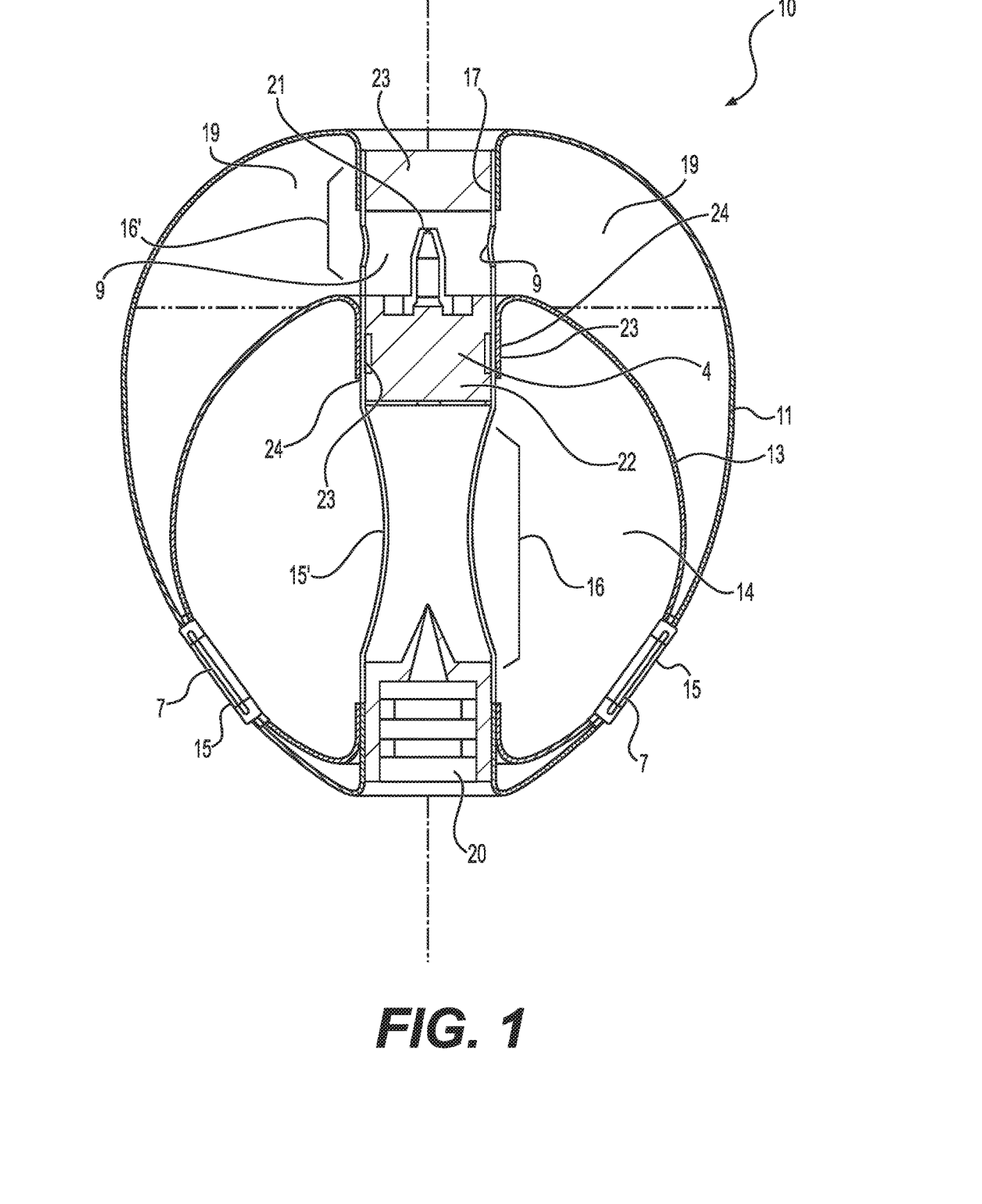
FIG. 1 shows a device for releasing one or more substances into a urinary bladder in accordance with one embodiment of the invention.

FIG. 1 shows a device 10 for releasing one or more substances in a urinary bladder, in accordance with one embodiment of the invention. The device 10 is shown in a longitudinal section in FIG. 1. The device 10 comprises an outer expandable balloon 11. The outer balloon 11 has a central conduit 9 extending along an axis A-A' of the device 10, so that the outer balloon 11 is essentially torroidal in shape. An inner expandable balloon 13 is located in the interior of the outer balloon 11 so as to define an annular inflation space 19 located between the outer balloon 11 and the inner balloon 13. The annular inflation space 19 is hereinafter referred to as a lumen 19. The inner balloon 13 also has a central conduit 4 extending along the axis A-A' which is thus coaxial with, and surrounds, the central conduit 9 of the outer balloon 10, so that the inner balloon 13 is essentially toroidal in shape. As mentioned, the inner and outer balloons 13,11 define the lumen 19 that is located between the inner and outer balloons 13,11. One or more conduits 15 extend from the interior of the inner balloon 13 to the exterior of the device 10 at a location where the inner balloon 13 and the outer balloon 11 are juxtaposed. Each of the conduits 15 is capped with a porous membrane 7. The device 10 further comprises a core tube 17 that is inserted into the conduit of the outer balloon 11, along the axis A-A'.

Inflation and/or pressurization of the outer balloon 11 and the inner balloon 13 is controlled/regulated by a plurality of valves that are installed at certain locations along a length of the core tube 17. The core tube 17 may define an interior pathway or channel having a first interior portion 16 at a first end of the core tube 17 and a second interior portion 16' at an opposite end of the core tube 17, where the first interior portion 16 is in fluid communication with an interior of the inner balloon 13 and the second interior portion 16' is in fluid communication with the lumen 19 (i.e., the annular inflation space). In the illustrated embodiment, the device 10 includes a first valve 20 and a second valve 21 disposed at opposite ends or sides of the core tube 17. More specifically, the first valve 20 is illustrated being disposed or located between the exterior of the device 10 and the first interior portion 16 of the core tube 17, and utilized to fill or inflate the inner balloon 13 to an inflated state. Also in this example, the second valve 21 is illustrated as being disposed between (i.e., separating) the first and second interior portions 16,16' of the core tube 17, and utilized to fill or inflate the lumen 19 to an inflated state and maintain that inflated state of the lumen 19. As illustrated, the first valve 20 is configured to control or regulate fluid communication between the exterior of the device 10 and the first interior portion 16 and the second valve 21 is configured to control or regulate the fluid communication to the second interior portion 16' as hereinafter described.

The inner balloon 13 serves to store particles, a solution or suspension containing one or more substances to be released into the urinary bladder. As explained below, the inner balloon 13 is filled from a syringe by inserting the syringe needle through the first valve 20 between the interior of the core tube 17 and the exterior of the device 10. The first valve 20 is hereinafter referred to as a suspension valve 20. As the particles, suspension or solution is injected into the core tube 17, it passes into the lumen of the inner balloon 13 via openings 15 in the wall of the core tube 17. The lumen 19, located between the inner balloon 13 and the outer balloon 11, serves to contain a fluid in order to endow the device 10 with a desired specific gravity. For example, in cases where the device 10 is to float on urine in the urinary bladder, the lumen 19 is filled with a liquid having a specific gravity less than that of urine, so that the specific gravity of the device 10 when deployed in the urinary bladder is less than the specific gravity of urine. To fill the lumen 19, a syringe needle is first inserted through the suspension valve 20, then through the core tube 17 and through the second valve 21. The second valve 21 is hereinafter referred to as a duckbill valve 21. The duckbill valve 21 is affixed to a cylindrical housing 22 that is immobilized inside the core tube 17 by means of a circumferential groove 23 that mates with a circumferential ring 24 on the inner surface of the core tube 17.

The device 10 may further comprise a retrieval magnet 23'.

The balloons 11 and 13 are made of a biocompatible polymer such as silicon or polyurethane. The balloons 11 and 13 are shown in FIG. 1 in their expanded, filled or inflated state. In the inflated state, the outer balloon 11 may have, for example, an ellipsoidal shape with a longitudinal axis L1 preferably of about 35 mm and a diameter D1 of preferably about 28 mm. The inner balloon 13, in its inflated state, may have for example, a spherical shape with a diameter D2 of about 26 mm and a volume V2 of about 10 cc. The core tube 17 is a rigid tube and has a length Lt of about equal to the diameter of the outer balloon 11 and an inner diameter Dt of about 3 to 5 mm.

Figure 2:
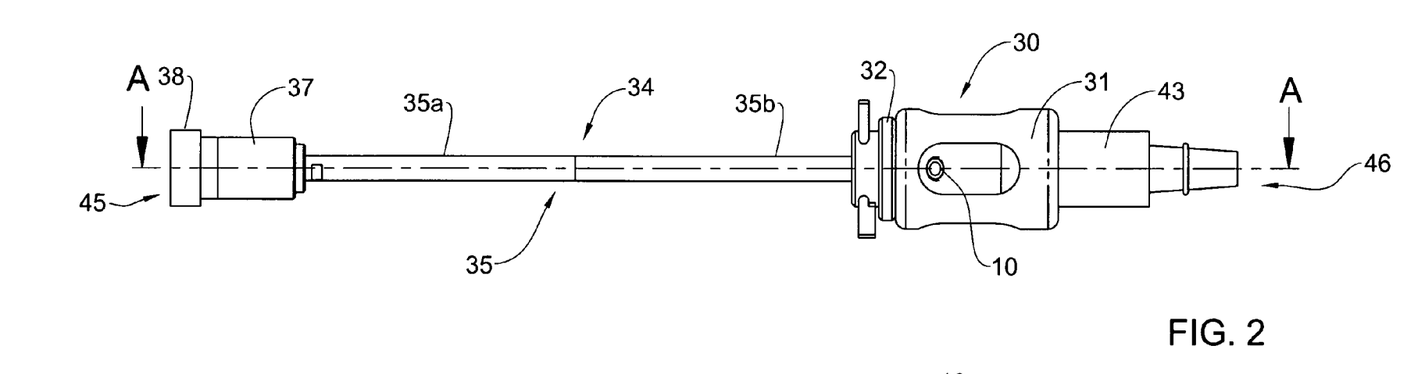
FIG. 2 shows an applicator for deploying the device of FIG. 1.
Figure 3:
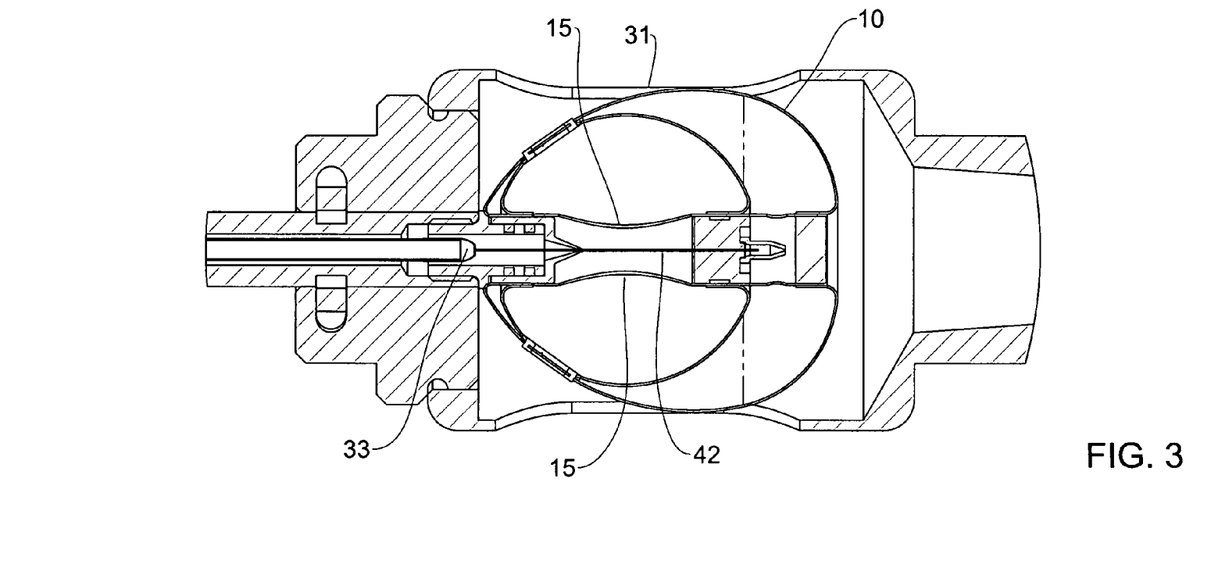
FIG. 3 shows the device housing of the applicator of FIG. 2.
Figure 4:
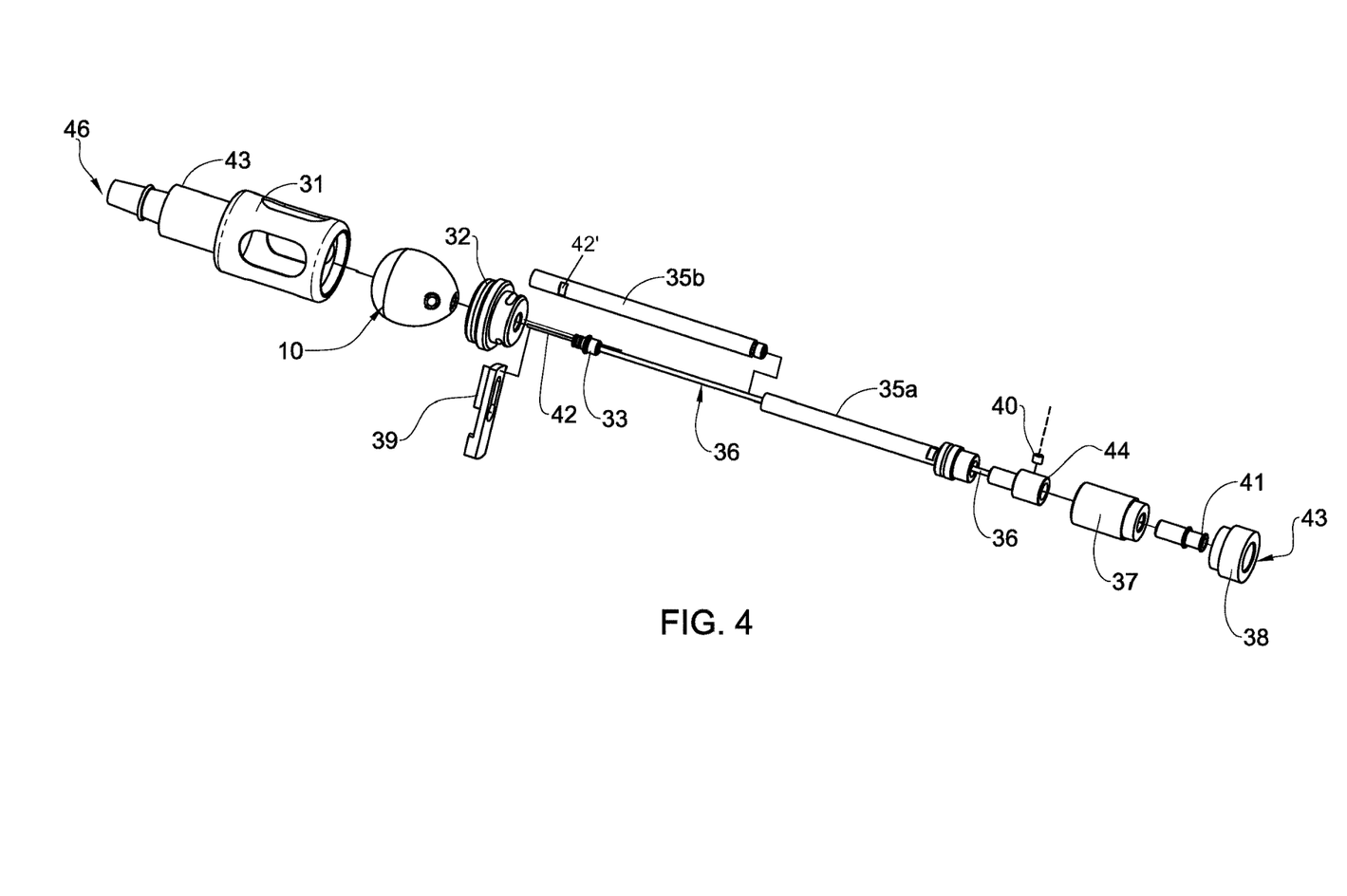
FIG. 4 shows an exploded view of the applicator of FIG. 2.

FIG. 2 shows an applicator 30 for deploying the device 10 in a urinary bladder. FIG. 4 shows an exploded view of the applicator 30. The applicator 30 has a proximal end 45 and a distal end 46. The applicator 30 has housing 31 shown in greater detail in FIG. 3. The applicator 30 has a housing 31 at its distal end that is dimensioned to receive the device 10. An insertion sheath 43 extends distally from the housing 31. The proximal opening of the housing 31 is closed by a flanged cover 32. The applicator 30 has a slender shaft 34 consisting of a cylindrical plunger 35 having a proximal portion 35a joined to a distal portion 35b, a needle 36 coaxial with the plunger 35, and a Teflon tube 42 attached to the needle 36 by a needle tip 33. At the proximal end of the needle 36 is a valve base 44 located inside a handle cover 37 that is connected to a Luer lock valve 41. A handle screw 38 immobilized in the flange 32 by a slidable locking stop 39 that is slidable between a locking position in which longitudinal translation of the plunger 35 is prevented due to engagement of the stop 39 and a pair of grooves 42' at the distal end of the plunger 35, and an unlocking position in which longitudinal movement of the plunger 35 is possible.

Figure 8:
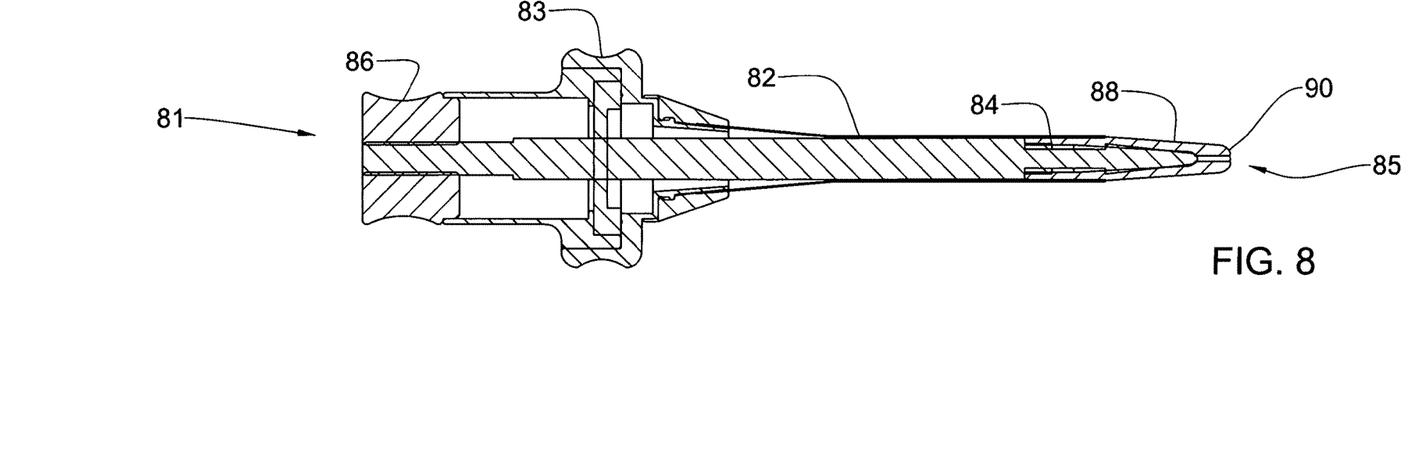
FIG. 8 shows a urethral module for facilitating insertion of an applicator into a urethra.

In order to facilitate insertion of the device 10 into a urinary bladder, a urethral module 80, shown in FIG. 8 is used. The urethral module 80 has a proximal end 81 and a distal end 85, an outer guiding tube 82 attached to a grasping handle 83. An elongated pivot 84 is inserted into the guiding tube 82. The pivot terminates in a conical tip 88 which has a coating 90 made of a soft rubber. A knob 86 attached to the pivot 84 is used to remove the pivot from the guiding tube 82, as explained below.

FIG. 5 shows a sequence of steps in a procedure for deploying the device 10 in a urinary bladder using the applicator 30. In FIG. 5*a*, the urethral module 80, with the pivot 84 inserted into the guiding tube 82, is inserted into a urethra 52 of a male or female individual until the distal end 92 of the guiding tube 82 is positioned into a urinary bladder 54. Then, as shown in FIG. 5*b*, the pivot 84 is withdrawn from the urethral module by grasping the handle 83 and the pulling on the knob 86, leaving the guiding tube 82 in the urethra.

Figure 5A:
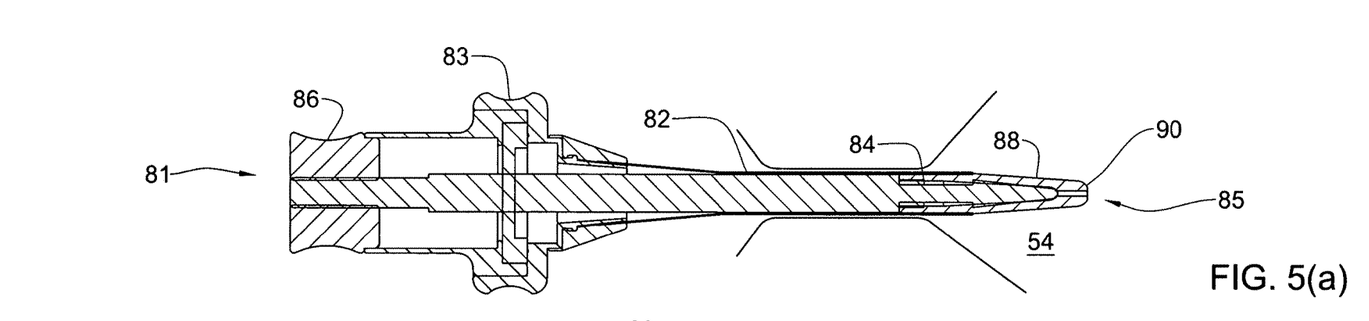
FIG. 5 shows a method of deploying the device of FIG. 1 in a urinary bladder using the applicator of FIG. 2.
Figure 5B:
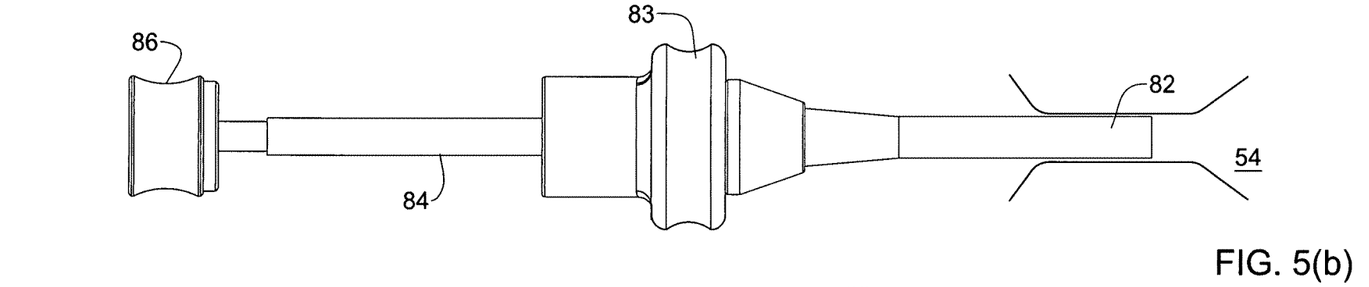
Figure 5C:
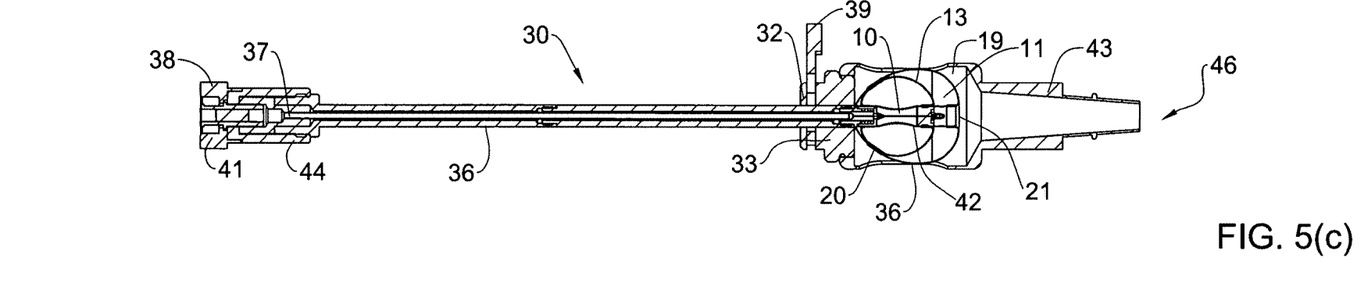
Figure 5D:
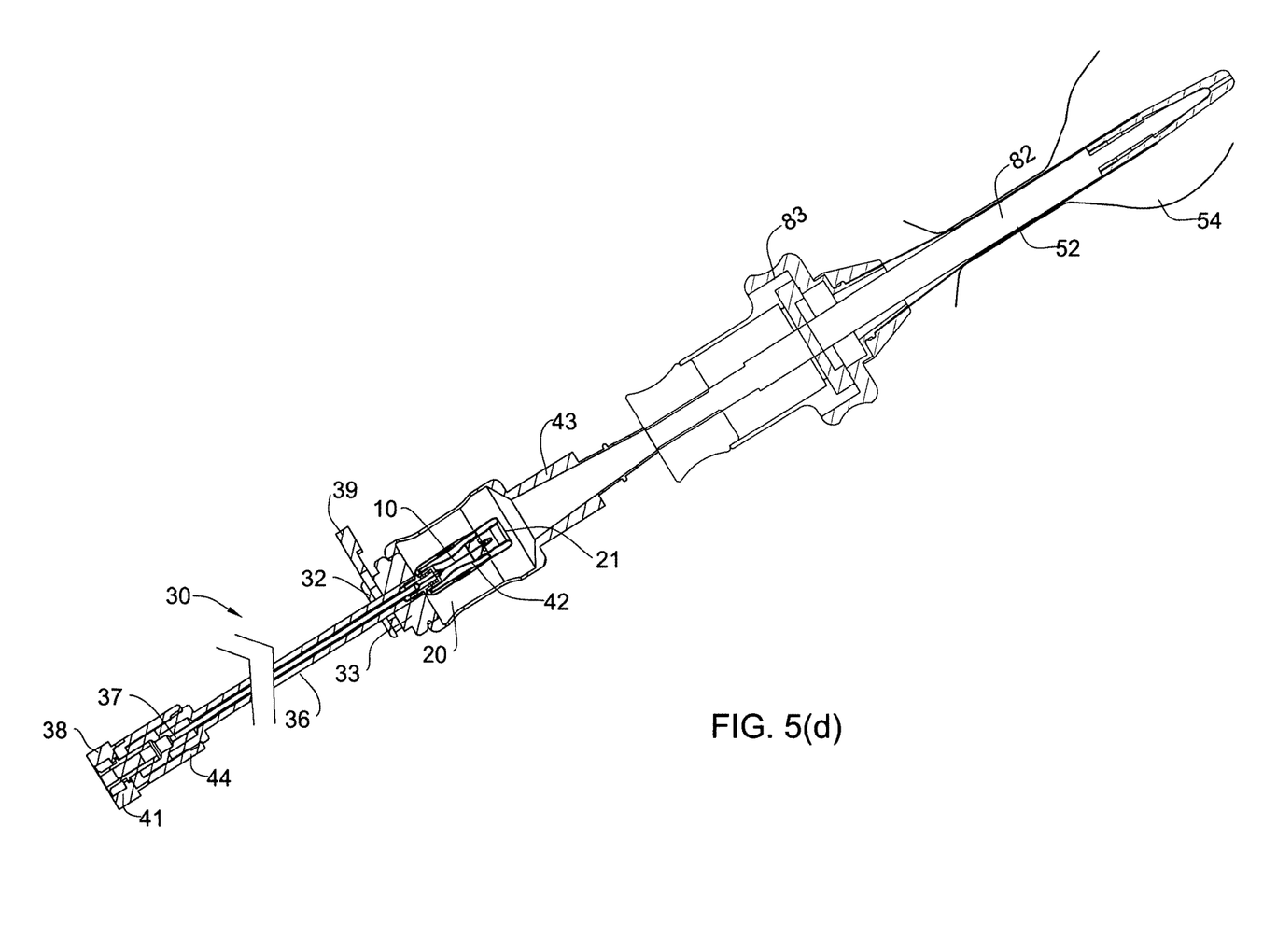

FIG. 5*c* shows the device 10 in its configuration during prolonged storage. The inner balloon 13 and the lumen 19 are both filled with air prior to mounting the device 10 into the housing 31, and the housing 31 is closed with the cover 32. The inner balloon 13 and the lumen 19 are maintained in the inflated state with air in order to prevent the walls of the inner or outer balloon from bonding during prolonged storage. The Teflon tube 42 at the distal end of the shaft is collapsed and inserted through an opening in the cover 32, through the suspension valve 20 of the device 10, the core tube 17 and the duckbill valve 21. The IN tip 33 is engaged in the suspension valve 20. The distal end of the plunger 35 is then locked by the locking stop 39. Just prior to deployment of the device 10 in a urinary bladder, the air is removed from the inner balloon 13 and the lumen 19 causing the device 10 to collapse into a narrow caliber conformation as shown in FIG. 5*d*. In this conformation, the insertion sheath 43 is connected to the proximal end of the guiding tube 82, as shown in FIG. 5*d*.

Figure 5E:
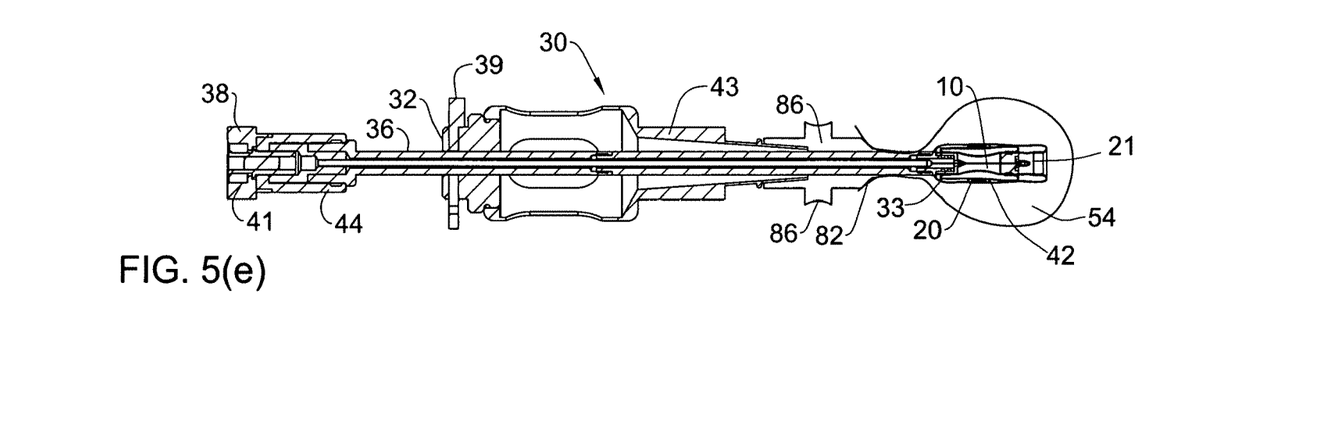

As shown in FIG. 5*e*, the stop 39 is brought to its unlocking position. The shaft is translated axially though the housing 32 causing the device 10 to enter and pass through the guiding tube 82. The shaft continues to be translated until the device 10 has entered the urinary bladder 54 as shown in FIG. 5*e*. The housing 31 is then translated proximally along the shaft as shown in FIG. 5*e*. The housing 31 continues to be translated until the housing 31 is adjacent to the valve base 44, as shown in FIG. 5*f*.

In one embodiment, axial movement of the housing 32 on the shaft is performed manually with the housing being grasped by the hand of the user and sliding the housing along the shaft. In another embodiment, translation of the housing is mechanized. For example, the device 10 may incorporate an electric motor (not shown) that drives the translation of the housing over the shaft. Alternatively, a hydraulic or pneumatic system may be used to translate the housing over the shaft. In the case of mechanized movement of the controller, the device may be provided with a controller to regulate the speed and direction of the housing. A ratchet mechanism may be used to prevent sliding of the housing in a distal direction.

Figure 5F:
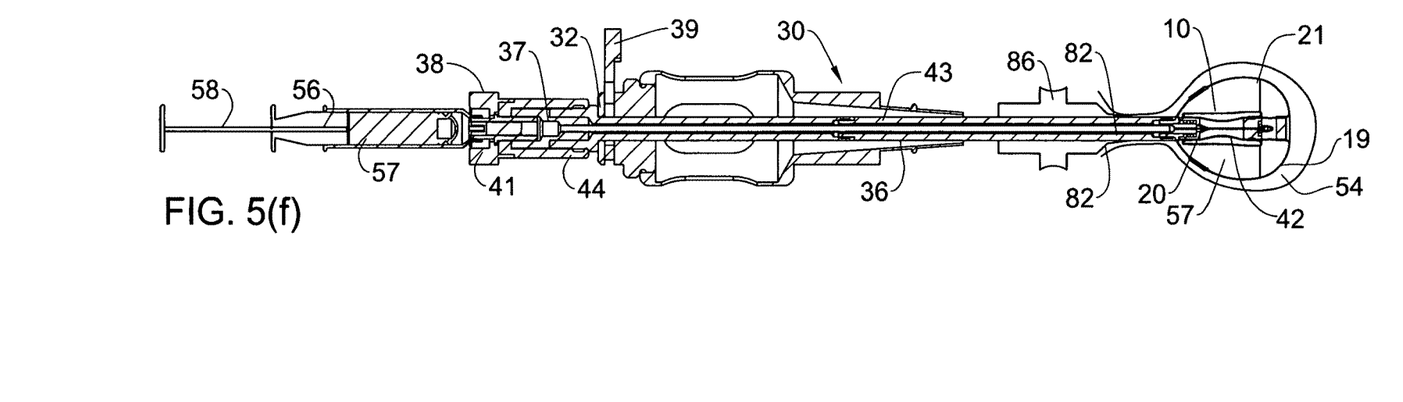

A syringe 56 is now attached to the Luer lock valve 41 at the proximal end of the applicator 30 (FIG. 5*f*). The syringe 56 contains the fluid 57 that is to fill the lumen 19 between the inner and outer balloons. As the plunger 58 of the syringe is depressed, the fluid 57 flows from the syringe 56 through the oil needle 36 and the Teflon tube 42 into the lumen 19. As the lumen 19 becomes filled with the fluid 57, the lumen 19 expands in the bladder 54.

The fluid 57 may be filled a biocompatible fluid such as air, water, saline or an oil such as liquid paraffin. The fluid is preferably pre-sterilized The fluid may have a specific gravity less than that of urine, such as mineral oil, to ensure a positive buoyancy of the device 10 in the bladder 54 so that the device 10 floats upon the urine and thus tends to remain away from the bladder exit.

Figures 5G, 5H:
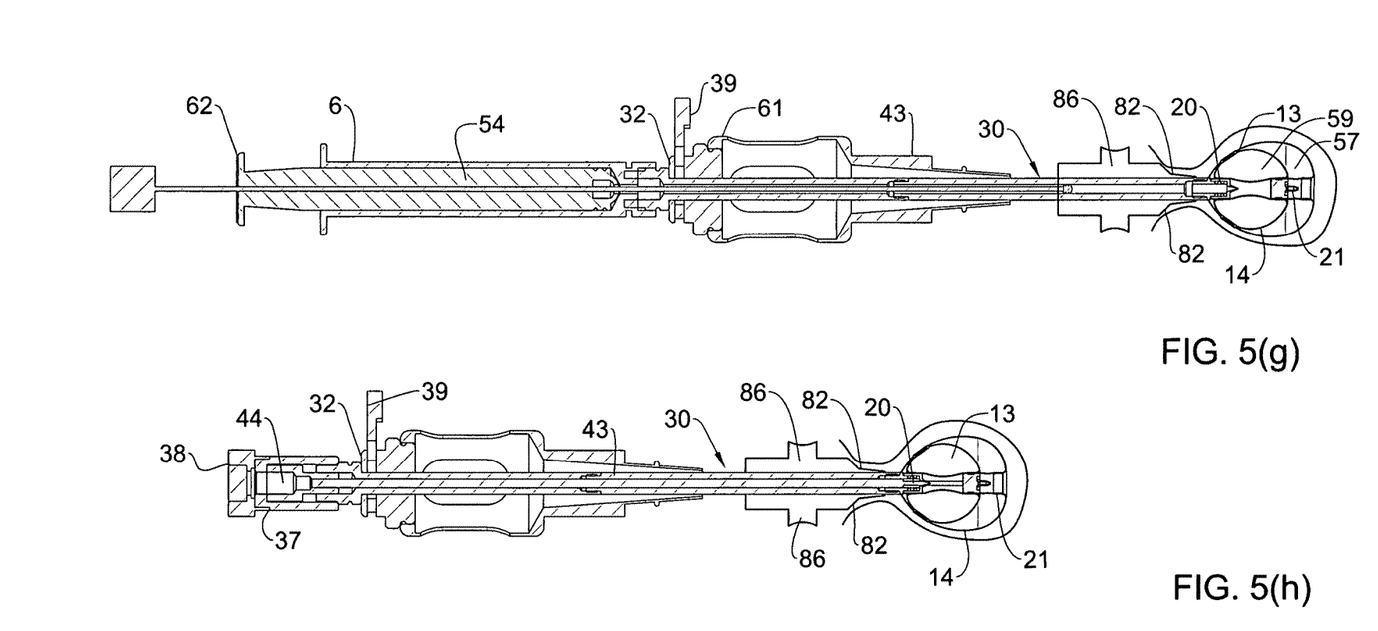

Referring now to FIG. 5*g*, the syringe 56 is detached from the applicator 30 together with the handle screw 38, the Luer lock valve 41, the handle cover 37, the valve base 44 and oil needle 36. Now, as shown in FIG. 5*g*, a second syringe 60, containing a fluid 59 that is to fill the inner balloon 13, is attached to the proximal end of the applicator 30 by inserting a needle 61 attached to the syringe 60 through the shaft 34 of the applicator 30 and the suspension valve 20. As the plunger 62 of the suspension syringe is depressed, the fluid 59 flows from the syringe 60, the needle 61 and the suspension valve 20 into core tube 17 and through the oval opening 15' into the inner balloon 13. As the fluid 59 fills the balloon 13, the balloon 13 expands.

In another embodiment (not shown), a "Y" shaped injecting adaptor is used. Each of the syringes 56 and 60 is attached to a different branch of the adaptor, and the stem of the adaptor is attached to the injection port of the device. In this way, the filling procedure can be simplified by eliminating the need to remove the syringe 56 and attach the syringe 60 during deployment of the device.

The fluid 59 may be a dry powder of small particles. In a preferred embodiment, the fluid 59 is a suspension containing particles of one or more substances to be released into the bladder. The particles can consist only of the substance or substances to be released, or the particles can consist of the substance or substances bound to a matrix. The particles can be dry, or encapsulated or embedded in a biodegradable or non-degradable material. The size of the particles and their concentration in the suspension is limited to allow the suspension to pass through the needle 61, such as a 16 G syringe needle. If the fluid 59 is a suspension, the suspension may be continuously stirred during injection in order to prevent sedimentation of the particles in the syringe (not shown). The suspension may continue to be injected into the inner balloon 13 after the lumen balloon 13 has attained its maximal volume. This creates a hydrostatic pressure inside the lumen 5 causing the suspension solvent to be extruded out from the inner balloon 13 through the conduits 15 and the dispensing membranes 7 into the bladder, while retaining the particles inside the inner balloon 13. This allows packing of the particles in the lumen 5 to a density that is larger than the original density of the particles in the suspension.

Figure 5I:
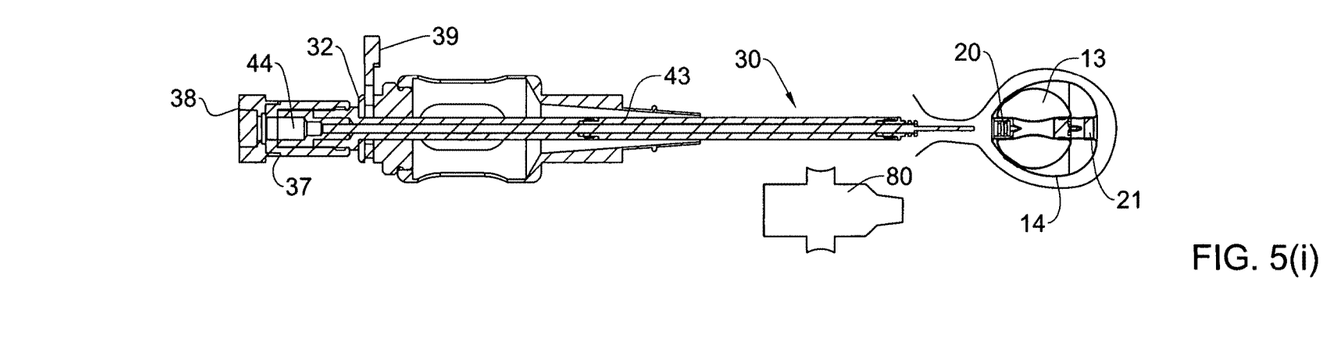

When filling of the inner balloon 13 is complete, the syringe 59 and its needle 61 are withdrawn from the valve applicator 30 and the valve base 44, handle cover 37 and the handle screw 38 are reassembled onto the proximal end of the applicator 30 (FIG. 5*h*). As the handle cover 37 is rotated, the device IN tip 33 disengages from the suspension valve 20, thereby releasing the device 10 in the bladder 54, as shown in FIG. 5*i*. The applicator 30 and the urthral module 80 may then be removed from the body leaving the device 10 in the bladder.

In the bladder, urine diffuses into the inner balloon 13 through the membranes 7 and conduits 15. The membranes 7 may be made for example from a hydrophilic polymer or a polymer coated with hydrophilic material and may have a pore size as required in any application. The urine activates the release of the drugs from the matrix in the fluid 59 and releases the substances contained in the particles. The substances diffuse in the urine through the conduits 15 and out of the device 10 and into the urinary bladder. The rate of substance release into the bladder typically depends on the initial size of the drug delivery particles, the properties of the matrix or encapsulation material and the size of the pores in the membranes 7. These parameters are preferably selected so that the release is constant and controlled over time.

The device 10 may optionally be configured to perform one or more additional functions in the bladder such as imaging the cavity, monitoring the cavity, or irradiating the cavity, for example as disclosed in WO 2004/041124.

When it is desired to remove the device 10 from the bladder 54, the balloons 11 and 13 may be punctured with a needle for suctioning the oil and the particles or to release their contents into the bladder. The device 10 may then be removed by using a retrieving device having a magnet configured to engage the retrieving magnet 23' on the device. The retrieving device disclosed in WO 03/075791, for example, may be used to retrieve the device 10.

Figure 6A:
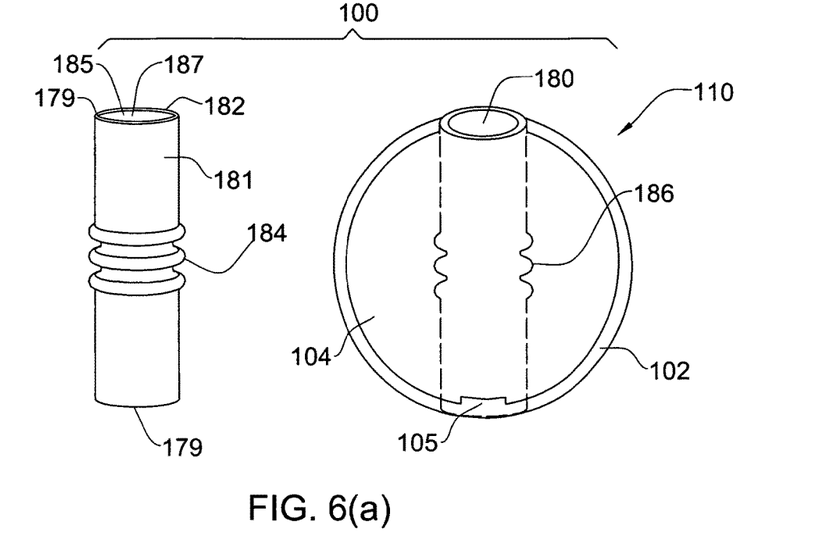
FIG. 6 shows a device for releasing one or more substances into a urinary bladder in accordance with a second embodiment of the invention.

FIG. 6a shows a device 100 for releasing one or more substances in a urinary bladder, in accordance with another embodiment of the invention. The device 100 includes a balloon 110 having a wall 102 made of a biocompatible material enclosing a lumen 104. The balloon 110 has a channel 180 that is generally cylindrical in shape. A self-sealing valve 105 in the wall of the balloon is used to fill the balloon with the fluid from a syringe.

Figure 6B:
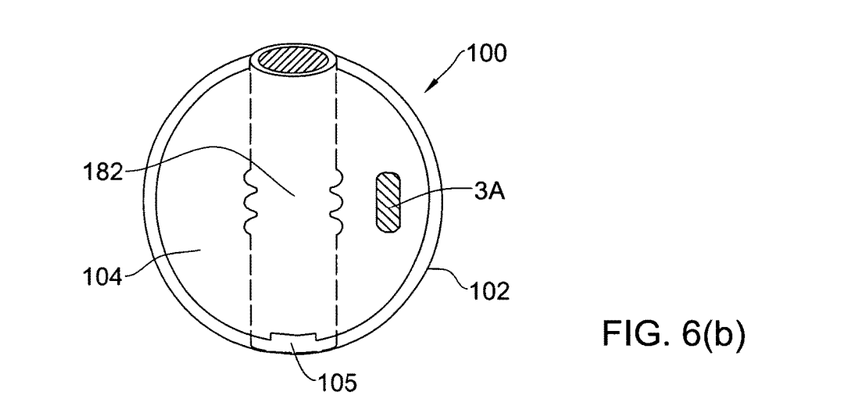

The device 100 also includes an insert 182. The insert 182 is an open-ended cylindrical shell surrounding a central passage way 187 and having outer dimensions selected to allow the insert 182 to be received in the channel 180, as shown in FIG. 6b. Grooves and ridges 184 on the external surface of the insert 182 increase the surface of the insert. Some of the grooves and ridges mate with complementary grooves and ridges 186 on the external surface of the wall 102 so as to retain the insert in the channel 180, and to prevent separation of the insert 180 from the balloon 110 during use of the device 100. The insert can be made of a biostable or biodegradable polymeric matrix.

The insert 182 contains a chamber 183 located between the interior wall 185 and the exterior wall 181 of the cylindrical shell. The chamber 183 is filled with a solution containing one or more substances to be released in the urinary bladder. At least a portion of the walls 181 and 183 and/or the ends 179 of the insert 182 is formed from a substance that is permeable to the substances to be released.

FIG. 6b shows the device 100 with the insert 182 inserted in the channel 180 of the balloon 110. The assembled device 100 may be deployed in a urinary bladder using the delivery device disclosed in WO2004/041124. After delivery of the assembled device, urine enters the passage way 187 of the insert. Substances stored in the chamber 183 can then diffuse out of the chamber 183 through the surface 185 and into the urine.

Figure 6C:
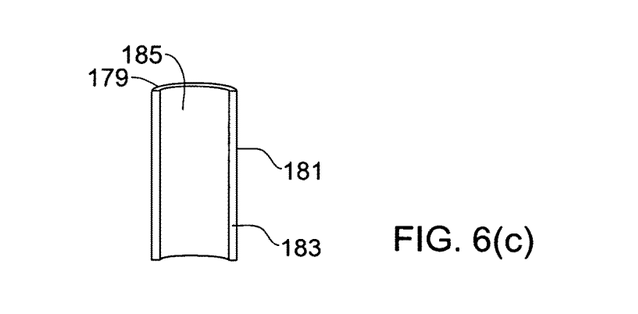

FIG. 6c, shows a cut away view of the insert 182. The inner surface 185 of the insert 182 has a surface area available for diffusion of the substances out of the chamber 183 that is significantly larger than the surface area that would be available for diffusion in a cylindrical insert having the same dimensions as the outer dimensions of the cylindrical shell of the insert 182, but in which only the end surface of the cylinder are available for diffusion. This allows a significantly faster rate of release than would occur with the cylindrical insert.

The device 100 may further comprise a magnetizable portion in order to facilitate retrieval of the device from the urinary bladder, as described below. The magnetizable portion may consist for example, of one or more metal particles that are associated with either the balloon 110 or the insert 182. The device 100 may be deployed in a urinary bladder using the retrieval device disclosed in WO2004/041124.

Figure 7A:
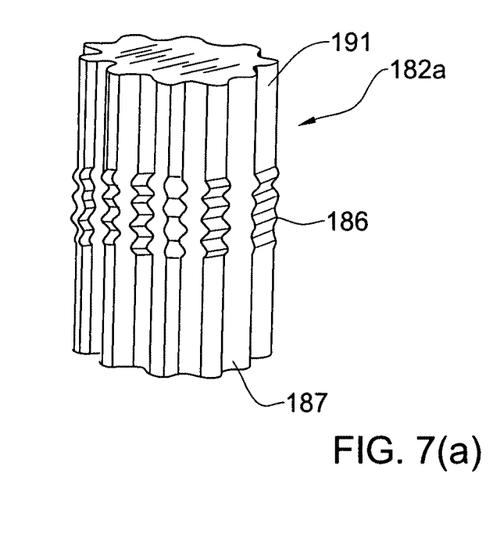
FIG. 7 shows an alternative insert for use in the device of FIG. 6.
Figure 7B:
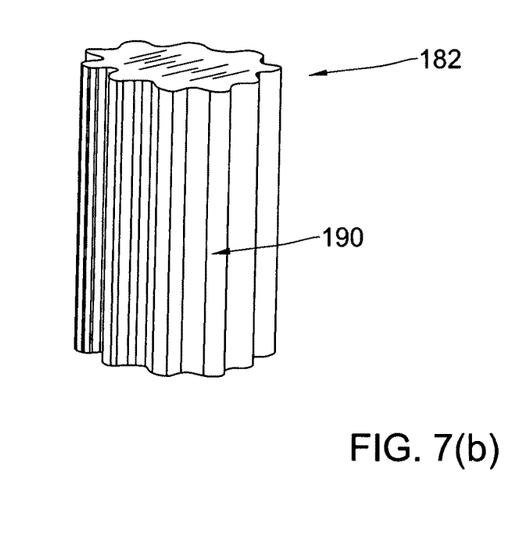

FIG. 7a shows an insert 182a that may be used in the device 100 instead of the insert 182. The insert 182a has a generally cylindrical shape that is dimensioned to be received in the channel 180. The insert 182 has grooves 186 that allow it to be retained in the channel 180 of the balloon 110. The insert 182a has a chamber 190 seen in the cut-away view of the insert 182a shown in FIG. 2b. The chamber 183 is filed with a solution of the substance or substances to be released into the urinary bladder. At least a portion of the wall 191 of the insert 182a is formed from a material that is permeable to the substance to be released.

The outer surface of the insert 182a has longitudinal grooves 187 that increase the surface area of the insert 182a in order to facilitate diffusion of substance from the chamber 190. The insert 182 with the stored substances is inserted into the channel 180 of the balloon 110. After delivery of the assembled device shown in FIG. 7c, urine enters the longitudinal grooves 187. Substance stored in the chamber 183 can then diffuse out of the chamber 190 through the wall 191 and into the urine.

The device 100 may optionally be configured to perform one or more additional functions in the bladder such as imaging the cavity, monitoring the cavity, or irradiating the cavity, for example as disclosed in WO 2004/041124.

The invention claimed is:

1. An implantable device having an exterior surface for releasing one or more substances into a body cavity, comprising:
    an outer balloon having a toroidal shaped interior surrounding and defining a central conduit of the outer balloon;
    an inner balloon located within the outer balloon so as to define an annular inflation space located between the outer balloon and the inner balloon, the inner balloon having a toroidal shape surrounding and defining a central conduit of the inner balloon, the central conduit of the outer balloon and the central conduit of the inner balloon being coaxial; and
    a core tube disposed within the central conduit of the outer balloon and the central conduit of the inner balloon, the core tube having a first interior portion that is in fluid communication with an interior of the inner balloon and a second interior portion that is in fluid communication with the annular inflation space located between the outer balloon and the inner balloon, the first and second interior portions being located at different locations along a length of the core tube, the core tube further comprising:
    a first valve located between an exterior of the device and the first interior portion of the core tube and configured to fill the inner balloon; and
    a second valve located along the length of the core tube at a location between the first interior portion of the core tube and the second interior portion of the core tube, the second valve configured to permit filling the annular inflation space located between the outer balloon and the inner balloon to an inflated state and maintaining the inflated state of the annular inflation space,
    wherein the first valve and second valve are coaxial and located at different locations along the length of the core tube.

2. The device according to claim 1, wherein the interior of the inner balloon is in fluid contact with the exterior surface of the device.

3. The device according to claim 2, wherein the fluid contact occurs via one or more conduits between the interior of the inner balloon and the exterior surface of the device.

4. The device according to claim 3, wherein the one or more conduits are covered with a porous membrane.

5. The device according to claim 1, dimensioned, to pass through a urethra when the outer and inner balloons are empty.

6. The device according to claim 1, further comprising a magnetizable portion.

7. A system for delivering one or more substances into a urinary bladder, comprising:
    the device according to claim 1; and
    a delivery catheter for delivering the device into a urinary bladder.

8. The system according to claim 7, further comprising the one or more substances to be released in the urinary bladder.

9. The system according to claim 8, wherein the one or more substances are contained in particles coated with a urine soluble coating.

10. The system according to claim 9, wherein the particles are coated in a biodegradable coating or capsule.

11. The system according to claim 9, wherein the particles are embedded in a matrix.

12. The system according to claim 8, wherein the one or more substances are dry drug particles soluble in urine.

13. A system for treating a urinary bladder of an individual, comprising:
    the device according to claim 1; and
    an applicator for inserting the device into the body.

14. The system according to claim 13, further comprising a retriever.

\* \* \* \* \*